(12) United States Patent
Ryll et al.

(10) Patent No.: US 9,370,343 B2
(45) Date of Patent: *Jun. 21, 2016

(54) INSTRUMENT TIP ASSEMBLY HAVING SELF-THREADING BACK HUB

(71) Applicant: MICROLINE SURGICAL, INC., Beverly, MA (US)

(72) Inventors: Paul David Ryll, Haverhill, MA (US); Peter Aliski, Malden, MA (US)

(73) Assignee: MICROLINE SURGICAL, INC., Beverly, MA (US)

( * ) Notice: Subject to any disclaimer, the term of this patent is extended or adjusted under 35 U.S.C. 154(b) by 7 days.

This patent is subject to a terminal disclaimer.

(21) Appl. No.: 14/287,290

(22) Filed: May 27, 2014

(65) Prior Publication Data

US 2014/0276668 A1  Sep. 18, 2014

Related U.S. Application Data

(60) Continuation of application No. 13/944,981, filed on Jul. 18, 2013, now Pat. No. 8,784,405, which is a division of application No. 13/451,046, filed on Apr. 19, 2012, now Pat. No. 8,529,555.

(51) Int. Cl.
*A61B 17/00* (2006.01)
*F16B 7/18* (2006.01)
*A61B 17/29* (2006.01)
*A61B 19/00* (2006.01)

(52) U.S. Cl.
CPC ........... *A61B 17/00234* (2013.01); *A61B 17/29* (2013.01); *F16B 7/182* (2013.01);
(Continued)

(58) Field of Classification Search
CPC ........... A61B 2019/4873; A61B 17/29; A61B 17/00234; A61B 2017/294; A61B 2017/2931; F16B 7/182; Y10T 29/19826; Y10T 29/19881; Y10T 403/68
See application file for complete search history.

(56) References Cited

U.S. PATENT DOCUMENTS 4,809,752 A * 3/1989 Strodter ...................... 138/96 T
5,810,879 A   9/1998 de Guillebon
(Continued)

FOREIGN PATENT DOCUMENTS

JP  56-063359   5/1981
JP  2005-073760  3/2005
(Continued)

OTHER PUBLICATIONS

European Search report of related application dated Jan. 9, 2015.*
(Continued)

*Primary Examiner* — Gary Jackson
*Assistant Examiner* — Boniface N Nganga
(74) *Attorney, Agent, or Firm* — Greenblum & Bernstein, P.L.C.

(57) ABSTRACT

A actuating instrument including an instrument tip assembly having a yoke attachment thread. The actuating instrument also includes an actuator having an actuating shaft. The actuating shaft is provided with a first thread within the actuating shaft and a second thread provided on the actuating shaft. Further, the first thread is connected to the yoke attachment thread. Additionally, a back hub is provided at a proximal end of the instrument tip assembly and includes a rib or ribs provided on one of an inner surface and an outer surface of the back hub. The rib or ribs projecting from the one of the inner surface and the outer surface of the back hub and engages the second thread of the shaft to from an attachment thread.

16 Claims, 7 Drawing Sheets

(52) U.S. Cl.
CPC ... *A61B2017/294* (2013.01); *A61B 2017/2931* (2013.01); *A61B 2019/4873* (2013.01); *Y10T 29/49826* (2015.01); *Y10T 29/49881* (2015.01); *Y10T 403/68* (2015.01)

(56) References Cited

U.S. PATENT DOCUMENTS

| | | | |
|---|---|---|---|
| 5,964,004 | A | 10/1999 | Bean |
| 7,122,028 | B2 | 10/2006 | Looper et al. |
| 8,025,621 | B2 | 9/2011 | Ewaschuk et al. |
| 2007/0027447 | A1 | 2/2007 | Theroux et al. |
| 2007/0073247 | A1 | 3/2007 | Ewaschuk |
| 2007/0078483 | A1 | 4/2007 | Ewaschuk et al. |
| 2007/0286700 | A1 | 12/2007 | Ladouceur |
| 2012/0083778 | A1 | 4/2012 | McGaffigan et al. |

FOREIGN PATENT DOCUMENTS

| | | | | |
|---|---|---|---|---|
| JP | 2005073760 | A | * | 3/2005 |
| JP | 2006-509169 | | | 3/2006 |
| JP | 2006509169 | A | * | 3/2006 |
| JP | 2007-29725 | | | 2/2007 |
| JP | 2007029725 | A | * | 2/2007 |
| JP | 2007-144122 | | | 6/2007 |
| JP | 2007144122 | A | * | 6/2007 |

OTHER PUBLICATIONS

Japan Search report of related application dated Feb. 28, 2014.*
Search report from E.P.O., mail date is Jul. 23, 2013.
Japan Official Action dated Feb. 25, 2014 and partial English translation thereof.

* cited by examiner

INSTRUMENT TIP ASSEMBLY HAVING SELF-THREADING BACK HUB

CROSS-REFERENCE OF RELATED APPLICATIONS

The present application is a continuation of U.S. application Ser. No. 13/944,981 filed Jul. 18, 2013 which is a division of U.S. application Ser. No. 13/451,046, filed Apr. 19, 2012, the disclosures of which incorporated herein by reference in their entireties.

BACKGROUND OF THE INVENTION

I. Field of the Invention

The present disclosure relates generally to an actuating instrument having an instrument tip assembly that is provided with a back hub and a method of connecting the instrument tip assembly to the actuating instrument. These actuating instruments are often used in technical fields that require a high degree of precision, e.g., precision cutting and grasping in a surgical environment, and precision cutting and grasping of wires or the like.

II. Discussion of the Background Art

In conventional actuating instruments (e.g., those used in surgical procedures or for any other type of implementation which requires precision usage) it is necessary to replace, e.g., cutting blades (intended for single-usage) with new and sharper blades, in which case it is economically feasible to merely remove the tip of the instrument and replace it with a new tip, rather than discarding the entire instrument.

The practice of reprocessing and reusing single-use devices (SUDs) has become increasingly more common because of costs savings and the reduction in waste. However, reprocessed SUDs, such as cutting blades, often do not function as well as SUDs that have not been reprocessed. For example, in the case of reprocessing a cutting blade, the blade may be damaged in the reprocessing process such that the cutting blade no longer cuts or opens and closes with the desired or required precision. Therefore, a reprocessed tip, such as those including a cutting blade, may not operate as well after reprocessing. Therefore, it is possible that any subpar operation of the reprocessed tip may be incorrectly attributed to the original manufacturer of the reprocessed tip, which may result in damage to the reputation of the original manufacturer.

Furthermore, in certain instances there are stigmas attached to reusing reprocessed devices and many users wish to avoid using reprocessed devices.

Additionally, actuating instruments such as cauterization tools, laparoscopes, electrified instruments (e.g., those used in a surgical environment) and the like which generally include a tube having a distal end onto which a tip is attached, the tip including a actuable tool for the medical procedure, surgical procedure, or other implementation to be performed, and a proximal end for connection to mechanical and/or electrical systems and which is operated by the surgeon or other technician performing a procedure or otherwise operating, have been widely used because the incision or opening necessary for insertion of such a tool on a actuating instrument is typically small in comparison to alternative methods. As a result of the relatively smaller incision, when used, e.g., in a surgical or medical environment, patients typically exhibit more rapid healing times and often experience fewer complications as a result of surgeries using such actuating instruments.

A typical actuating instrument of this class may include at least two detachable portions—the tip having the actuable tool as one of the detachable portions, and the tube leading from the distal end back to the proximal end as the other. Further, such actuating instruments may include an inner tube leading from the proximal end to the tube end of the tube at the distal end for connecting to a yoke which is part of the detachable tip. Because proper operation of the tool on the tip may require precise mechanical shifting of the inner tube and yoke in relation to the tube and housing of the tip, one method that has been used to provide the necessary differentiation when connecting the tip to the tube end has been the use of two sets of threading with mutually differential pitches, respectively on the connections between the yoke of the tip and the inner shaft of the tube end on the one hand, and a housing or casing of the tip and an outer tube of the tube end, on the other hand.

As a result, however, as shown in FIG. 5 of the conventional art, the two threadings of different pitches require fine machining during the manufacturing process, within tolerances that are difficult to achieve using automation and which may tend to increase the cost of manufacturing of such actuating instruments or medical devices. For example, after an initial machining of the threading, it may be necessary to test and make adjustments several times by hand, which requires skilled machinists as well as additional iterative steps, which increase the time for manufacture considerably. Furthermore, the use of threading requires the surgeon or medical technician performing a procedure with the actuating instrument or medical device to intricately align the two threadings of different pitch when assembling the tip to the tube end. Such an operation may increase the time necessary to detach and/or reattach tips to tube ends during, e.g. a medical procedure or any other implementation and therefore increase the costs and risks associated with the medical procedure or other implementation.

SUMMARY OF THE INVENTION

The present disclosure provides a self-threading feature on a back hub of a tip assembly to indicate or ensure single-usage of the tip assembly and prevent or eliminate the ability to reprocess the tip assembly. Further, the self-threading feature eliminates the need for precision threaded connecting threads (i.e., which connect the tip assembly to the remainder of the actuating instrument) that are currently machine molded in the back hub and the intricacies associated therewith.

These and other features of the present disclosure will be apparent from review of the specification and accompanying drawings.

Accordingly, a non-limiting embodiment of the present disclosure provides an actuating instrument (e.g., a surgical or other mechanical instrument) having an instrument tip assembly. The instrument tip assembly may include a yoke attachment thread. Further, the actuating instrument may include an actuator having an actuating shaft. In this regard, the actuating shaft may have a first thread provided within the actuating shaft and a second thread provided on the actuating shaft. The first thread may be connected to the yoke attachment thread. Additionally, a back hub may be provided at a proximal end of the instrument tip assembly. Further, the back hub may have a rib or ribs provided on one of an inner surface and an outer surface of the back hub and the rib or ribs may project from the one of the inner surface and the outer surface of the back hub. Accordingly, the rib or ribs may engage the second thread of the shaft to form an attachment thread.

In an additional feature, the rib or ribs may include a plurality of longitudinal extending projections that are spaced apart from each other in a circumferential direction of the back hub. Also, the rib or ribs may include a plurality of circumferentially extending and longitudinally spaced projections provided, e.g., on an inner or an outer surface of the back hub.

In another feature, the rib or ribs may deform upon engagement with the second thread to form the attachment thread. Further, an actuable tool may be provided at a distal end of the instrument tip assembly.

In a further aspect, each of the plurality of longitudinal extending projections may be semicircular in cross-section. Additionally, the plurality of longitudinally extending projections may be equally spaced apart in the circumferential direction of the back hub.

In an additional aspect, the second thread may be provided as an exterior thread provided on an outer surface of the actuating shaft and the rib or ribs may project inwardly from the inner surface of the back hub to engage the exterior thread and form the attachment thread. In this respect, the inner surface of the back hub may be configured to receive the exterior thread. Additionally, the rib or ribs may comprise a plurality of circumferentially extending projections that are spaced apart from each other in a longitudinal direction of the back hub. Furthermore, the rib or ribs may comprise a plurality of longitudinal extending projections that are spaced apart from each other in a circumferential direction of the back hub.

Additionally, the second thread may be an internal thread provided within the actuating shaft at a front end of the first thread and the rib or ribs may project outwardly from the outer surface of the back hub to engage the internal thread and form the attachment thread. In this respect, the internal thread may receive at least a portion of the back hub that is provided with the outwardly projecting ribs.

BRIEF DESCRIPTION OF THE DRAWINGS

The present disclosure is further described in the detail description which follows, in reference to the noted plurality of drawings, by way of non-limiting examples of preferred embodiments of the present disclosure, in which like characters represent like elements throughout the several views of the drawings, and wherein.

DETAILED DESCRIPTION

The particulars shown herein are by way of example and for purposes of illustrative discussion of the embodiments of the present disclosure only and are presented in the cause of providing what is believed to be the most useful and readily understood description of the principles and conceptual aspects of the present disclosure. In this regard, no attempt is made to show structural details of the present disclosure in more detail than is necessary for the fundamental understanding of the present disclosure, the description taken with the drawings making apparent to those skilled in the art how the several forms of the present disclosure may be embodied in practice.

Figure 1A:
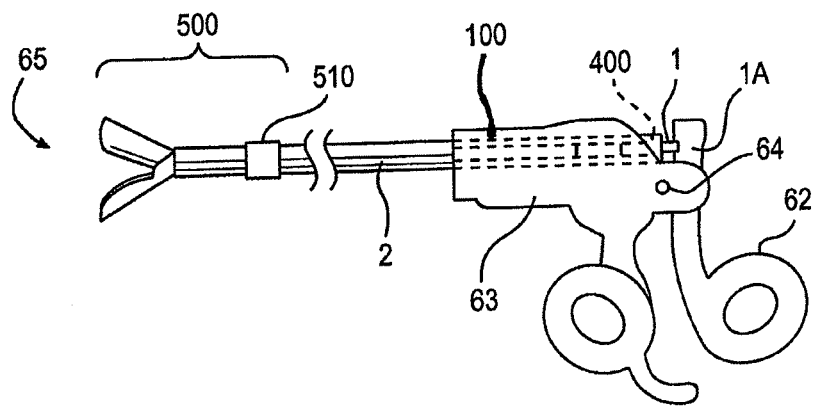
FIG. 1A is a side view of an actuating instrument according to a non-limiting embodiment of the present disclosure.

Referring to FIG. 1A, the actuating instrument may include an actuator 62 having an actuating shaft 100. In this regard, the tool 505 may open and/or close (or may be otherwise operated) by the movement of the inner shaft 100 relative to the tube 2. For example, an actuator and actuator shaft may be actuated as described in commonly-assigned U.S. Pat. No. 5,358,508, the entire contents of which are expressly incorporated by reference herein.

Figure 1B:
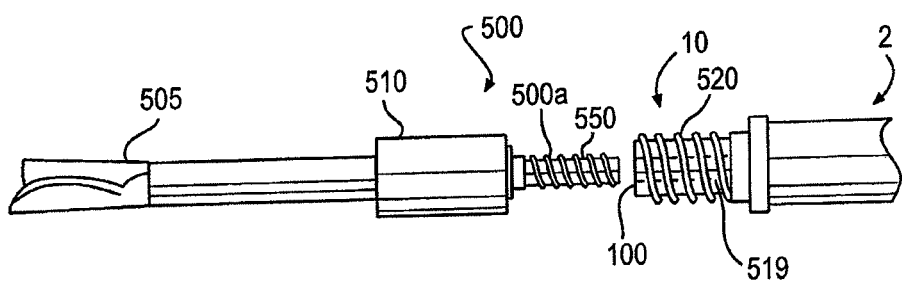
FIG. 1B is a side view of a tip assembly of the actuating instrument.
Figure 2A:
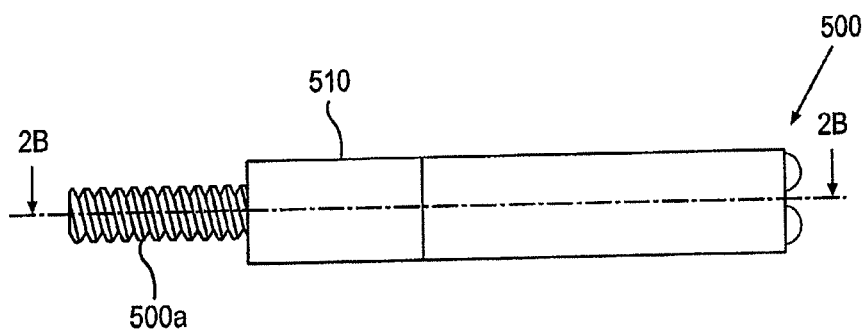
FIG. 2A is a plan view of the instrument tip assembly.
Figure 2B:
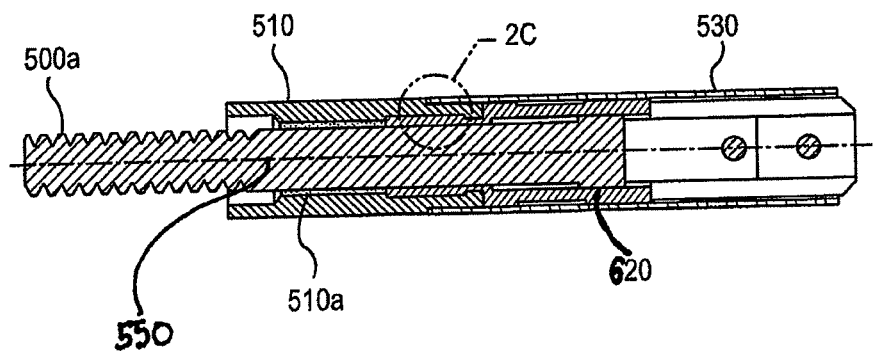
FIG. 2B is a sectional view of the instrument tip assembly of FIG. 2A taken along A-A.
Figure 2C:
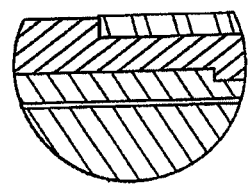
FIG. 2C is an enlarged view of the detail C of FIG. 2B.

Referring to the drawings, as shown in FIG. 2A-2C, the instrument tip assembly 500 may include a yoke attachment thread 500a and the actuating instrument may include an actuator 62 having an actuating shaft 100. In this regard, the actuating shaft 100 (as shown by the dotted lines in FIG. 1) may have a first thread 519 (as shown by the dotted line in FIG. 1B), e.g., an interior thread provided on an inner surface of the actuating shaft 100 and a second tread 520, e.g., an exterior thread, as shown in FIG. 1B, provided on an outer surface of the actuating shaft 100.

In this regard, the first 519 and second threads 520 may be formed of any suitable material. For example, a hard plastic or thermoplastic material or any other suitable metal capable of establishing a threaded connection.

The first thread 519 of the actuating shaft 100 may be connected to the yoke attachment thread 500a. For example, the first thread of the actuating shaft 100 may be screwed onto the attachment thread 500a provided on an outer surface of the yoke 550. The yoke 550 may be received within a yoke support 620. The instrument tip assembly may be provided with an outer covering 530 surrounding the support 620 and a portion of the back hub 510. See FIG. 2B.

Additionally, a back hub 510 may be provided at a proximal end of the instrument tip assembly 500, as shown in FIGS. 1A through 2C. Further, the back hub 510 may have one or more ribs 510a provided on one of an inner surface or an outer surface of the back hub 510 and the rib or ribs 510a may project from the one of the inner surface and the outer surface of the back hub 510. See FIGS. 3a-3d. The rib or ribs 510a may engage the second thread (e.g., an exterior thread) 520 of the shaft to from an attachment thread.

For example, the exterior thread (when provided as the second thread 520) may be provided on an outer surface of the actuating shaft 100 and the rib or ribs 510a may project inwardly from the inner surface of the back hub 510 to engage the exterior thread 520 and form the attachment thread. Accordingly, the inner surface of the back hub 510 may be configured to receive the exterior thread 520. See FIG. 3A.

Furthermore, the rib or ribs 510a may be formed integral with the back hub 510 and made of the same material as the material of the back hub 510.

In another aspect of the disclosure, the rib or ribs 510a may be unitarily or integrally formed with the back hub 510 and made of a different material or of a same material having a different hardness. Additionally, the rib or ribs 510a may be formed by injection molding or extrusion molding. Furthermore, the rib or ribs 510a may be formed of any suitable material capable of being deformed by the material of the exterior thread.

The rib or ribs 510a may deform upon engagement with the exterior thread 520 to form the attachment thread. In this regard, the rib or ribs 510a may be plastically (i.e., such that the rib or ribs cannot return to its original form prior to engagement with the exterior thread) or elastically deformed as the rib or ribs 510a progressively engages the exterior thread 520 of the shaft 100. For example, when attaching the tip assembly 500 to the actuating shaft 100, the threads on the yoke 550 may engage the actuating shaft threads (i.e., the interior threads not shown), thereby drawing the back hub 510 towards a proximal end of the actuating shaft 100. This action forces the exterior threads 520 to engage the rib or ribs 510a in the back hub 510 creating the attachment thread, thereby providing a secure coupling to the hand piece during use.

Further, as shown in FIGS. 3a-3d, the rib or ribs may include a plurality of longitudinal extending projections (or plurality of ribs) that are spaced apart from each other in a circumferential direction of the back hub.

Accordingly, upon engagement of the exterior threads 520 with the rib or ribs 510a, the rib or ribs may be deformed such that a plurality of rib segments is formed in each rib or ribs 510a. In this regard, each of the plurality of rib segments may be interposed within the space between corresponding adjacent threads of the exterior threads 520, thereby forming an attachment thread. Thus, in accordance with the present disclosure, the rib or ribs 510a may extend generally perpendicular to a diametrical direction of the exterior threads 520.

Accordingly, because the attachment thread may be formed as the tip assembly 500 is attached to the hand piece 62 and the rib or ribs 510a may be plastically deformed, the back hub 500 cannot be reattached with the same security to the actuating instrument upon removal.

Thus, the present disclosure prevents reprocessing the tip assembly 500. That is, since the rib or ribs 510a may be plastically deformed to provide the attachment threads, when the tip assembly 500 is removed from the actuating instrument the rib or ribs will no longer be able to securely attach the tip assembly 500 to the actuating instrument, thereby eliminating impermissible or undesirable reuse of the tip assembly 500. That is, the present disclosure ensures single usage of an intended SUD.

In other words, the actuating instrument of the present disclosure may be configured so as to provide a secure connection by progressively deforming previously un-deformed rib or ribs that are brought into engagement with exterior threads. Therefore, upon removal of the tip assembly 500 from the actuating instrument the rib or ribs will have been deformed due to the previous engagement with the exterior threads. Thus, it would be difficult or impossible to reestablish a secure connection between the tip assembly 500 and the exterior threads 520 by, e.g., attempting to screw the yoke attachment of the tip assembly onto the exterior threads of the actuator shaft, thereby effectively limiting the tip assembly 500 to a single use.

Further, a surgical tool 505 or any other tool may be provided at a distal end of the instrument tool assembly. Among the various surgical tools which may be part of the tip are, for example, electrified scalpels, shears, grasping tools, cauterization tools, laparoscopic tools, and the like.

Figure 3A:
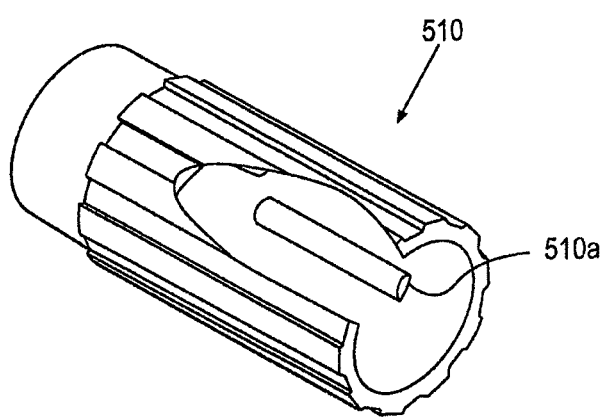
FIG. 3A is a partial cutaway perspective view of the back hub of the accordingly to a non-limiting embodiment of the present disclosure.
Figure 3B:
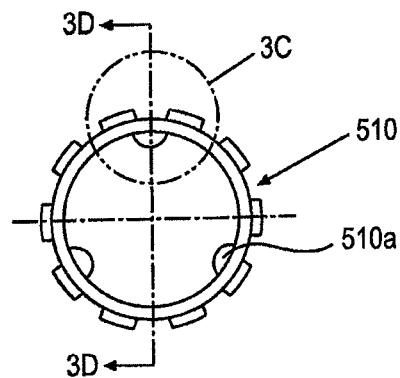
FIG. 3B is a cross-section of the back hub taken in a direction perpendicular to a longitudinal axis of the back hub.
Figure 3C:
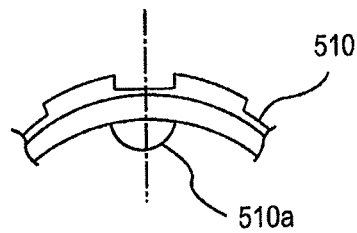
FIG. 3C is an enlarged view of the detail A in FIG. 3B.
Figure 3D:
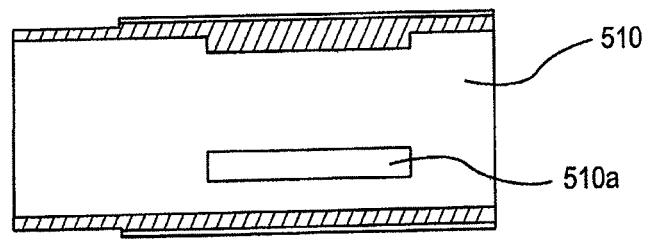
FIG. 3D is a sectional view of the back hub of FIGS. 3A and 3B, taken along B-B in FIG. 3B.
Figure 4A:
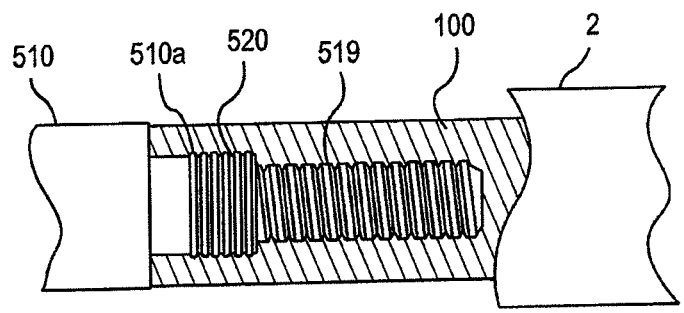
FIG. 4A is a perspective view of another non-limiting embodiment of the back hub according to the present disclosure.
Figure 4B:
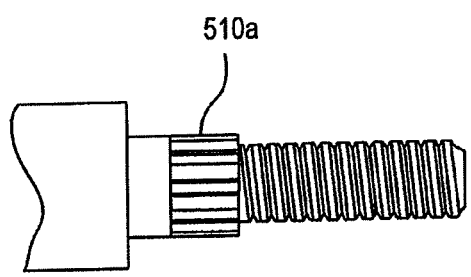
FIG. 4B is a perspective view of yet another non-limiting embodiment of the back hub according to the present disclosure.
Figure 5:
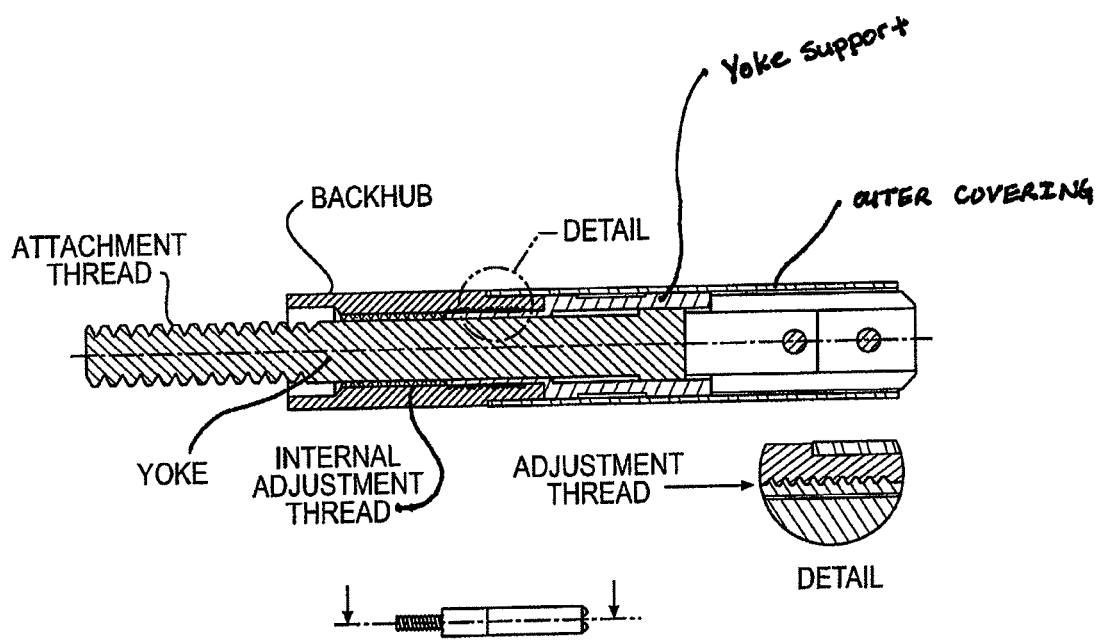
FIG. 5 is an instrument tip assembly in accordance with the related art.

In a further aspect, each of the plurality of longitudinal extending ribs or projections may be semicircular in cross-section, as shown in FIG. 3c. Additionally, the plurality of longitudinally extending ribs may be equally spaced apart in the circumferential direction of the back hub, as shown in FIG. 3b Further, the second thread 520 may be provided as an internal thread within the actuating shaft 100 at a front end of the first thread 519 and the rib or ribs 510a may project outwardly from the outer surface of the back hub 510 to engage the second thread (e.g., the internal thread) 520 and form the attachment thread. In this respect, the internal thread 520 may receive at least a portion of the back hub 510 that is provided with the outwardly projecting ribs 510a. See FIG. 4A. Additionally, the rib or ribs may comprise a plurality of circumferentially extending projections 510a that are spaced apart from each other in a longitudinal direction of the back hub 510. See FIG. 4A. Furthermore, the rib or ribs may comprise a plurality of longitudinal extending projections 510a that are spaced apart from each other in a circumferential direction of the back hub. See FIG. 4B.

Further, when the rib or ribs are provided on an outer surface of the hub this aspect provides easy viewing and determination of whether the tip assembly has been previously used. That is, since the markings or deformation of the rib or ribs 510 caused by engagement with the thread 520 will be readily apparent. Further, it should be appreciated, that unless otherwise noted, other operations and features in each embodiment may be the same or similar.

However, one of ordinary skill in the art would readily recognize that any suitable feature for establishing the connections may be employed without departing from the spirit of the present disclosure.

It is further noted that the foregoing examples have been provided merely for the purpose of explanation and are in no way to be construed as limiting of the present disclosure. While the present disclosure has been described with reference to a preferred embodiment, it is understood that the words which have been used herein are words of description and illustration, rather than words of limitation. Changes may be made, within the purview of the appended claims, as presently stated and as amended, without departing from the scope and spirit of the present disclosure in its aspects. Although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims.

What is claimed is:

1. An actuating instrument, comprising:
    an instrument tip assembly having a yoke attachment thread;
    an actuator having an actuating shaft, the actuating shaft having a first thread provided within the actuating shaft and a second thread provided on the actuating shaft, and wherein the first thread is connected to the yoke attachment thread; and
    a back hub provided at a proximal end of the instrument tip assembly, the back hub having a rib provided on one of an inner surface and an outer surface of the back hub,
    wherein the rib projects from the one of the inner surface and the outer surface of the back hub,
    wherein the second thread is provided in a shape so as not to mate with the rib, wherein the rib engages the second thread of the shaft to form an attachment thread, and wherein the rib deforms upon engagement with the second thread to form the attachment thread.

2. The actuating instrument according to claim 1, wherein a surgical tool is provided at a distal end of the instrument tip assembly.

3. The actuating instrument according to claim 1, wherein the second thread is an exterior thread provided on an outer surface of the actuating shaft and the rib projects inwardly from the inner surface of the back hub to engage the exterior thread and form the attachment thread, the inner surface of the back hub receiving the exterior thread.

4. The actuating instrument according to claim 1, wherein the second thread is an internal thread provided within the actuating shaft at a front end of the first thread and the rib projects outwardly from the outer surface of the back hub to engage the internal thread and form the attachment thread, the internal thread receiving a portion of the back hub that is provided with the outwardly projecting ribs.

5. An instrument tip assembly for an actuating instrument, the instrument tip assembly comprising:
   a yoke attachment thread provided at a proximal end of the instrument tip assembly, the yoke attachment thread configured to be connected to a first thread provided within an actuating shaft of an actuator of an actuating instrument;
   a back hub provided at a proximal end of the instrument tip assembly, the back hub having a rib provided on one of an inner surface and an outer surface of the back hub,
   wherein the rib projects from one of the inner surface and the outer surface of the back hub, and wherein the rib is configured to engage with a second thread provided on the actuating shaft to form an attachment thread,
   wherein the second thread is provided in a shape so as not to mate with the rib, and wherein the rib deforms upon engagement with the second thread to form the attachment thread.

6. The instrument tip assembly according to claim 5, wherein a surgical tool is provided at a distal end of the instrument tip assembly.

7. The instrument tip assembly according to claim 5, wherein the back hub and the rib are formed integrally and of a same material.

8. The instrument tip assembly according claim 7, wherein the material of the back hub has a greater hardness than the material of the rib.

9. The instrument tip assembly according to claim 5, wherein the back hub and the rib are formed integrally and of a different material.

10. The actuating instrument according to claim 5, wherein the second thread is an exterior thread provided on an outer surface of the actuating shaft and the rib projects inwardly from the inner surface of the back hub to engage the exterior thread and form the attachment thread, the inner surface of the back hub receiving the exterior thread.

11. The actuating instrument according to claim 5, wherein the second thread is an internal thread provided within the actuating shaft at a front end of the first thread and the rib projects outwardly from the outer surface of the back hub to engage the internal thread and form the attachment thread, the internal thread receiving a portion of the back hub that is provided with the outwardly projecting ribs.

12. A method of assembling an actuating instrument, the method comprising:
   providing an instrument tip assembly having a yoke attachment thread;
   providing an actuator having an actuating shaft, the actuating shaft having a first thread provided within the actuating shaft and second thread provided on the actuating shaft;
   providing a back hub at a proximal end of the instrument tip assembly, the back hub having a rib provided on one of an inner surface and an outer surface of the back hub, wherein the rib projects from the one of the inner surface and the outer surface of the back hub, and wherein the second thread is provided in a shape so as not to mate with the rib;
   screwing the first thread onto the yoke attachment thread such that the back hub is drawn towards a proximal end of actuating shaft and the rib progressively engages the second thread of the shaft, thereby deforming the rib to form an attachment thread.

13. The method of assembling the medical device according to claim 12, wherein the rib is plastically deformed.

14. The actuating instrument of claim 1, wherein the actuating instrument comprises a medical device.

15. The instrument tip assembly of claim 5, wherein the instrument tip assembly is configured to be used in a medical device.

16. The method of assembling the actuating instrument of claim 12, wherein the actuating instrument comprises a medical device.

* * * * *